United States Patent
Chikawa

(10) Patent No.: US 7,688,943 B2
(45) Date of Patent: Mar. 30, 2010

(54) METHOD FOR EVALUATING PHYSICAL CONDITIONS USING HEAD HAIR OR BODY HAIR

(76) Inventor: Jun-ichi Chikawa, 8-12, Nishinogawa 1-chome, Komae-city, Tokyo (JP) 201-0001

( * ) Notice: Subject to any disclaimer, the term of this patent is extended or adjusted under 35 U.S.C. 154(b) by 152 days.

(21) Appl. No.: 11/660,239

(22) PCT Filed: Aug. 10, 2005

(86) PCT No.: PCT/JP2005/014627

§ 371 (c)(1),
(2), (4) Date: Feb. 13, 2007

(87) PCT Pub. No.: WO2006/016597

PCT Pub. Date: Feb. 16, 2006

(65) Prior Publication Data

US 2007/0258561 A1 Nov. 8, 2007

(30) Foreign Application Priority Data

Aug. 13, 2004 (JP) ............................. 2004-236197

(51) Int. Cl.
*G01N 23/223* (2006.01)
*G01T 1/36* (2006.01)
(52) U.S. Cl. .................. 378/48; 378/45; 378/44
(58) Field of Classification Search ............ 378/44–49, 378/210; 702/19, 22, 27, 28, 30; 436/63, 436/64, 79, 172
See application file for complete search history.

(56) References Cited

U.S. PATENT DOCUMENTS 5,073,913 A * 12/1991 Martin ........................ 378/34

5,610,071 A * 3/1997 Sabal ........................... 436/79
2003/0134271 A1 * 7/2003 Martin ............................ 435/5

(Continued)

FOREIGN PATENT DOCUMENTS

JP 2004-45133 2/2004

OTHER PUBLICATIONS

Kubo, Hideo, A Simple Method of X-ray Fluorescence Analysis in Hair, 1981, Physical Medical Biology (IOP), vol. 26, No. 5, pp. 867-874.*

(Continued)

*Primary Examiner*—Edward J Glick
*Assistant Examiner*—Anastasia Midkiff
(74) *Attorney, Agent, or Firm*—William L. Androlia; H. Henry Koda

(57) ABSTRACT

Elemental concentrations in hair (head and body hair) and dried serum have been measured by x-ray fluorescence analysis using synchrotron radiation. The relative concentration defined by log P–log S are obtained from the fluorescent spectra, where P is the peak height for the element and S is the background height. The observation shows that hair has two separate [Ca] concentration levels, the upper level and lower level. Since the content in hair growing at a steady state must be equal to the supply from serum, the upper and the lower level of hair [Ca] are attributed to open and close Ca ion channels of the hair matrix cells and can be derived from the serum concentrations of Ca ion and Ca atoms included in serum protein, respectively. The hair analysis is useful for cancer detection and protection as well as for diagnosing the Ca metabolism.

2 Claims, 12 Drawing Sheets

U.S. PATENT DOCUMENTS

2003/0223536 A1* 12/2003 Yun et al. .................. 378/45

OTHER PUBLICATIONS

Schwenka, Julie, PharmD, Elevated blood calcium level (Hypercalcemia), Aug. 3, 2003, University of California, San Francisco, www.cancersupportivecare.com, pp. 1-3.*

Chan, June M, et al., Dairy products, calcium, and prostate cancer risk in the Physicains' Health Study, 2001, American Journal of CLinical Nutrition, vol. 74, pp. 549-554.*

Rogers, Mary A. M., et al. A Case-Control Study of Element Levels and Cancer of the Upper Aerodigestive Tract, Jul./Aug. 1993, Cancer Epidemiology: Biomarkers & Prevention, vol. 2, pp. 305-312.*

* cited by examiner

METHOD FOR EVALUATING PHYSICAL CONDITIONS USING HEAD HAIR OR BODY HAIR

TECHNICAL FIELD

The present invention relates to a method for evaluating physical conditions which diagnoses the health condition of a subject by measuring the content of a specific element in hair, and furthermore relates to the method for evaluating physical conditions which diagnoses the health condition of the subject by measuring the concentration of the specific element for the subject and comparing it with the concentration of healthy person.

BACKGROUND ART

Modern society holds various problems and health is also one of them. At the present age when scientific technology progressed, we have received the benefit of new substances, but we are also exposed to the attack of harmful reaction of the new substances. Since the number of affections such as allergic diseases as a typical modern disease increases rapidly, it is inferred that there is a limitation in maintaining health. Therefore, in order to live in modern society healthfully, it becomes important to know always our health condition and to know early the abnormalities of health condition.

As the simple methods for evaluating the physical conditions, it has been generally performed to evaluate from complexion of a subject or from the condition of one part of body such as skin. In fact, the condition of complexion or skin shows the quality of current health. However, by these evaluation approaches, the quality of the physical conditions cannot be known clearly, and it is unknown when the abnormal condition has occurred. Therefore, it is required to present an evaluation method to know the change of physical conditions objectively and moreover to know the occurrence times of abnormalities not only at present but also in past.

Although physical conditions are changing daily, it is rare to notice its change, so it is desired to express the change of the physical conditions by quantifying objectively. In order to quantify the change of the physical conditions objectively, the extracted blood etc. must be analyzed. The result of analysis shows the contents of elements that constitute the blood at this instant and cannot show variations based on time progress. Therefore, even if it becomes clear that the result of inspection is unusual, the outbreak time or elapsed time of the abnormality is unknown. On the other hand, blood has the role that maintains homeostasis, so that the abnormalities are not shown in many cases even when it is unhealthy. Moreover, great costs are needed for extracting and analyzing the blood.

The body consists of 29 kinds of elements, and since its most part is water, hydrogen occupies more than one half (60.3%), oxygen 25%, carbon 10.5%, nitrogen 2.4%, so that these four kinds of elements occupy 98.2%. The trace elements other than said elements are inorganic, and they are generally called minerals such as iron, copper, calcium and magnesium. Therefore, if these trace elements, especially level changes in trace elements making important roles in life activities are analyzed, the change of physical conditions can be known promptly and it will become possible to adopt the effective countermeasures.

Especially, although calcium is an important element that constitutes the frame of body, it plays other important roles besides this. For example, calcium element is contained in cell membrane, so that it stabilizes the structure of this membrane, and the permeability of membrane is maintained. Moreover, calcium element is a neurotransmitter relating to stimulus and contraction of muscle, and also relates to stimulus and secretion function of exocrine gland and endocrine gland.

In particular, when calcium is deficient, bony calcium begins to dissolve into blood, and it is going to keep the calcium concentration in blood at the homeostatic level. Simultaneously, calcium ion inflows takes place and the intracellular calcium concentration is raised up, even though calcium is deficient so that functions of the cells deteriorate. In general, this is called "calcium paradox".

FIG. 15 is a diagram illustrating "calcium paradox". The axis of abscissa expresses Ca concentrations of bone, blood serum and cytosol, and the axis of ordinate expresses the molar quantity. Calcium not only becomes the ingredient of the frame of body, but is carrying out very important roles for the body. One of them is a role of signal transmitter in nerve. Therefore, the calcium concentration [Ca] in blood balances with bony calcium concentration, and is strictly controlled to be at the homeostatic value (0.1 g in blood 1 L). Hereafter, the unit of liter is written by L.

FIG. 15A) is a conceptual diagram showing the calcium concentrations of normal state contained in bone, blood and inside of cell. The bony calcium concentration [Ca] is 10000 times [Ca] in blood serum, and the intracellular calcium concentration is 1/10000 times the [Ca] in blood serum; it is seen that calcium hardly exists in cell. Therefore, cell can quickly react to concentration change of calcium being the signal transmitter, and can make the normal work based on this reactivity.

FIG. 15B) is a conceptual diagram showing the calcium concentration in aging or calcium shortage condition. When calcium level in blood is down, calcium begins to dissolve into blood from bone being the huge storehouse of calcium, the calcium concentration in blood tends to be at the homeostatic level to maintain the neural transmission operation normally. At the same time, a cell becomes full of calcium like a Ca flood into a cell, so that function of cell deteriorates because of worsening of signal transmission by calcium, then the Ca flood causes various illnesses such as not only osteoporosis but also immunity disease, diabetes, hypertension, malignant tumor, and arteriosclerosis. As described above, in spite of calcium shortage, the phenomenon in which intracellular calcium concentration rises is apparently a contradictory phenomenon, so it is called "calcium paradox."

FIG. 16 is a diagram showing the system by which the calcium concentration [Ca] in blood is controlled to be at the homeostatic value. When [Ca] in blood increases, calcitonin is secreted from the thyroid gland, and calcium in blood (blood serum) is deposited in bone. On the other hand, when [Ca] in blood decreases, parathyroid hormone (PTH:Parathyroid Hormone) is secreted from the parathyroid gland, and calcium is extracted from bone into blood. PTH controls the excretion of calcium to urine by acting on kidney, and promotes the absorption of calcium from intestines by activating vitamin D. Thus, PTH increases [Ca] in blood, at the same time, makes overflow of calcium in cells in the whole body scale, and becomes the cause of "calcium paradox".

Although "calcium paradox" is apparently the contradictory phenomenon, it can be understood that calcium plays very important roles in life activity of human body. Therefore, if it can be diagnosed by a simple method whether calcium is deficient, changes of physical conditions can be predicted, and it can be used for a sick omen or a sick progress. If the concentration of PTH in blood is measured, it can be diagnosed whether calcium is deficient, but the concentration of PTH changes with a one-day cycle, and a PTH molecule is broken easily into its fragments. Moreover, since its fragments also function, measurement is not easy. As it is necessary to extract and inspect blood samples for that purpose, it has not been used widely until now because of time and cost.

It has been considered so far that there are individual differences in content of an element contained in hair and content of an element varies depending on place and time of taking hair even for the same person's hair. In order to obtain content of an element in hair, hairs of several grams were taken, and the content of each element was analyzed and obtained by atomic absorption analysis etc. However, this method measures an average value of contents of the element in hair, and the measured value is an average value at least for one month. Since the content of an element changes more quickly, it is a disadvantage that the value at the measurement time is unknown.

Also, X-ray fluorescence analysis is desirable for measuring content of each element in hair. In X-ray fluorescence analysis an electron beam or X-ray beam irradiates a sample, the generated fluorescent X-rays having the wavelength peculiar to the element is detected, and the kind and amount of elements contained in the sample are obtained. However, since the wavelength of the irradiated X-rays in the conventional method spreads widely, it overlaps with the wavelength of the generated fluorescent X-rays, so that the high sensitivity is not obtained because of the noise, so exact analysis has been difficult.

Furthermore, since the fluorescent X-rays intensity is proportional to the mass of element within the excitation beam, the data obtained depend upon hair thickness and shape. Therefore, although absolute measurement of concentration to know how much mg of the element is contained in 1 g of hair is required, it is difficult to measure the mass of the irradiated part precisely for each sample.

As a result of studying deeply for above-mentioned problem, the present inventor paid his attention especially to the hair root of head hair or body hair on the basis of assumption that "calcium paradox" due to shortage of calcium occurs similarly in every cell in the living body. Head hair or body hair is supported by hair root, and the nutrient is supplied from hair matrix cells wrapping the hair root. Therefore, when measuring the amount of calcium in this hair root, it is surmised that the shortage of calcium could be known and the research was repeated wholeheartedly.

Consequently, the present inventor proposed the diagnostic method of physical conditions based on head hair or body hair by Japanese Patent Laid-Open No. 2004-45133 (patent reference 1), and made an oral announcement of the contents of said patent reference 1 in English in the international congress of Ritsumeikan University for two days of Jan. 12 and 13 of 2004. This diagnostic method is characterized in that many trace elements contained in hair root of head hair or body hair are detected and then the content ratios among elements are calculated.

[Patent Reference 1] Japanese Patent Laid-Open No. 2004-45133

DESCRIPTION OF THE INVENTION

Problems to be Solved by the Invention

Said patent reference 1 aimed at solution of the above-mentioned problems through the steps of irradiating the synchrotron radiation X-rays to hair root of head hair or body hair, measuring contents of the elements contained in the hair root, and obtaining the content ratios of elements.

FIG. 17 is a spectrum diagram of the content of element contained in a hair root in the patent reference 1. Photon Energy (keV) is expressed with an axis of abscissa, and Intensity (arbitrary unit) is expressed with an axis of ordinate. The detected elements are calcium (Ca), iron (Fe), copper (Cu), zinc (Zn), lead (Pb), bromine (Br) and strontium (Sr). The pulses generated at photon energy (wavelength) proper to an element are accumulated, and the accumulated amount is expressed as fluorescent X-ray intensity for the proper photon energy of the element. Since the fluorescent X-ray intensity is proportional to the content of the element, the ratio of observed intensity to the fluorescent X-ray intensity of a standard element of the same person is obtained and is expressed as a content of the element.

In said patent reference 1, although the contents of elements are obtained by using the iron (Fe) content contained in the hair root of head hair or body hair as a standard, it cannot be concluded that the content of iron in the hair root has always the same value, and its contents are different among individuals. Therefore, the diagnostic method using the content ratio is unsatisfactory in accuracy. The diagnosis by comparison with the content ratio of the element for other healthy person also is not enough in accuracy.

Moreover, the patent reference 1 is limited to hair root of head hair or body hair, and is characterized by measuring the content of element in a hair root. Since a hair root is covered with hair matrix cells, it is thought that the change of physical conditions is reflected clearly. However, content of element contained in a hair root is the content at present time, and is not the content in past days. Therefore, as the hair root analysis of head hair or body hair described in the patent reference 1 can give only the variation of the content of element at present time, the exact diagnosis of physical conditions cannot be performed.

As a result of research by the present inventor, it is proposed that concentration can be derived precisely as a relative value by a logarithmic expression of the content of element instead of the content ratio among elements, and it is concluded that measurement by analyzing an arbitrary part of head hair or body hair can give the concentration of element at that time point. Consequently, it is discovered that the important elements such as calcium, iron, copper, zinc and selenium etc. contained in hair are controlled to have their homeostatic concentrations which are taken as their standards for healthy persons, so that the present invention is completed.

Therefore, the purpose of the present invention is to provide a method to know the concentration homeostasis in hair for healthy persons and to make improvement of dietary habits and cancer screening by evaluating physical conditions as deviations from said homeostasis.

Means for Solving the Problem

The present invention is done to know physical conditions at the past, and the first form of the present invention is a method for evaluating physical conditions by measuring concentrations of an element contained in an arbitrary point of head hair or body hair.

The second form of the present invention is the method for evaluating physical conditions, wherein concentrations of element contained in two or more points of head hair or body hair are measured, and a time change in concentration of the element is derived by comparing the measured concentrations of the element.

The third form of the present invention is the method for evaluating physical conditions, wherein the evaluation of physical conditions is performed by the use of one or more head hairs or body hairs taken periodically.

The fourth form of the present invention is the method for evaluating physical conditions, wherein the evaluation of physical conditions is performed by comparing concentrations of elements in head hair or body hair with concentrations of the elements contained in other specimens aside from hair taken from the same person.

The fifth form of the present invention is the method for evaluating physical conditions, wherein concentration of element contained in head hair or body hair of a subject is compared with concentration of the element contained in head hair or body hair of healthy persons, and physical conditions are evaluated to be abnormal when said concentration of the element of said subject is larger or smaller than that of healthy persons.

The sixth form of the present invention is the method for evaluating physical conditions, wherein the evaluation is made using the concentration of the element that is derived from content of the element in a measured part of head hair or body hair.

The seventh form of the present invention is the method for evaluating physical conditions, wherein a part of head hair or body hair is irradiated with an excitation x-ray beam, fluorescent x-rays emitted from the part are measured, and concentration of an element is derived from the fluorescent X-ray intensity.

The eighth form of the present invention is the method for evaluating physical conditions, wherein fluorescent X-ray intensity peak height (P) from an element is expressed by the decimal logarithm (log P) and concentration of the element is given by the value (log P–log S) obtained by deducting the background height (log S) independent of the kind of element.

The ninth form of the present invention is the method for evaluating physical conditions, wherein concentration of the element for a subject is written as subject concentration (log P–log S), concentration of the element for healthy persons is written as healthy person concentration (log P–log S)$_{st}$, the normalized concentration M is defined by the formula $$\log M = (\log P - \log S)/(\log P - \log S)_{st}.$$

The evaluation for physical conditions is performed by said normalized concentration M.

The tenth form of the present invention is the method for evaluating physical conditions, wherein the element to be measured is a trace element such as Ca, Fe, Cu, Zn, Se, Sr and Rb.

The eleventh form of the present invention is the method for evaluating physical conditions, wherein the excitation beam of x-ray fluorescence analysis is synchrotron radiation.

The twelfth form of the present invention is the method for evaluating physical conditions, wherein evaluation is a diagnosis of breast cancer.

The 13th form of the present invention is the method for evaluating physical conditions, wherein the evaluation is performed together with medical detailed examination.

Effect of the Invention

According to the first form of the present invention, concentrations of elements contained in an arbitrary part of head hair or body hair can be measured, so that the physical conditions can be evaluated. In the patent reference 1, the analysis was performed only for hair root of head hair or body hair. Therefore, since the content of element in hair root is the content of element at the present, only the present physical conditions become clear from the result of evaluation. The present invention was completed through paying attention to that the concentration of element at the present can be measured by analyzing the hair root of head hair or body hair and that analyzing an arbitrary part of the hair can give the concentration of element at the past. Since head hair or body hair is growing from the hair root, the arbitrary part reflects the concentration of element of the hair root at a past time. Therefore, if the arbitrary part of hair is analyzed, the concentration of element at the corresponding time can be measured, and if the hair root is analyzed, the present concentration of element can be measured, so that it is possible to know change of physical conditions dating back to the past time. As a result, since the method for evaluating physical conditions of the present invention can know the time to make change of the physical conditions, it can be used for knowing a sick omen or a sick progress. Moreover, since head hair or body hair is a solid, it is easy to handle, it is optimal for analyzing the concentration of element, and it is easy to perform a lot of diagnosis periodically. Therefore, the evaluation of physical conditions by head hair or body hair is a very effective diagnostic approach.

According to the second form of the present invention, concentrations of element contained in two or more points of head hair or body hair are measured, and a time change of concentration of the element can be derived by comparing the measured concentrations of the element. Therefore, the record in the past by analysis of one hair, namely the hysteresis information on concentration of element can be investigated easily. Analysis of the hair root gives the present information, and the information in the past can be analyzed along hair shaft toward the hair tip. Since a hair length of 1 cm corresponds to about one month, the tip point at 12 cm apart from the hair root gives information one year ago. Consequently, even if there is no abnormality in concentration of element at the present, it not only can be investigated whether there were certain abnormalities in the past, but the time elapsing from an abnormal occurrence and the time variation in concentration of element can be known, so that the information becomes important for diagnosing a sick omen and a sick progress.

According to the third form of the present invention, since the evaluation of the physical conditions can be performed by using of one or more head hairs or body hairs extracted periodically, it is possible to obtain not only the hysteresis information on concentration of element contained in hair at the present but also the hysteresis information in the past. The hysteresis information on concentration of element contained in one hair depends on its length. Long hair has the information for a long term and short hair has the information for a short term. Therefore, if hairs are periodically extracted according to their lengths, the change of physical conditions over a very long term can be investigated, so that the time to produce abnormalities in the physical conditions can be known precisely. Consequently, the cause of the abnormalities in physical conditions can be traced and used for the daily health care and sick protection. Moreover, if the time interval for taking hair is shortened, it is possible to avoid the change of the content of element in hair due to chemicals contained in hair cosmetics etc., so that reliable information can be obtained. Moreover, trace elements contained in hair dye move into hair. For example, since calcium has the tendency to move into hair and to form pair atoms of calcium in hair, the effect of hair dye can be deduced.

According to the fourth form of the present invention, the evaluation of physical conditions is performed by comparing concentrations of an element of head hair or body hair with those of the element contained in other specimen besides hair from the same person. By using the method for evaluating physical conditions of the present invention, it gets possible to know not only deviations from the healthy concentration value of an element contained in hair but the relation with the concentration of the element contained in other specimens besides hair such as blood and tissue pieces of the same person, so that more reliable diagnosis can be performed. Therefore, as to concentration abnormalities of element in hair, when their origin cannot be identified only from the concentration of a specific element contained in hair, the purpose can be attained by employing the relation with the concentration of the element contained in other specimens of the same person.

According to the fifth form of the present invention, when the measured concentration of element of a subject is larger or smaller than the concentration of element of healthy persons, the physical conditions are evaluated to be abnormal. The present inventor discovered that the concentration of an element in hair of healthy persons is controlled to be at the homeostatic level, and has the value to be common for healthy persons. By proposing to detect change of physical conditions promptly by deviations from this homeostasis, the present invention is completed. Therefore, since concentrations of an element of a subject are almost the same during a healthy period, it can be found that there is a certain abnormality when large or small compared with this homeostatic value. It can be used for sick prophylaxis by investigating causes of the abnormality.

According to the sixth form of the present invention, since the measured content of element is the total number of atoms in the measured part of head hair or body hair, similarly to concentration it can be compared with content of element contained in other specimens from the same person and healthy person, and proportionality between them can be investigated. The thickness of the measured head hair or body hair varies from sample to sample, resulting in different masses or molar quantities as a content of element even for healthy person. Then, in this case, the concentration of element is adopted as a content of element, and for example, if the element mass per unit mass of hair is taken, they must be mostly in agreement among healthy persons. Therefore, by comparing the concentration of element for the subject with healthy concentration, a reliable evaluation of physical conditions becomes possible. It is possible to evaluate precisely the physical conditions from the relation of the concentration of element of head hair or body hair with the concentration of element contained in other specimens from the same person and healthy persons besides head hair or body hair.

According to the seventh form of the present invention, since the concentration of element can be derived by measuring of fluorescent X-rays emitted from the measurement part of head hair or body hair, the exact concentration of element can be obtained. In X-ray fluorescence analysis, although it is desired to analyze the samples for comparison under the conditions as same as possible, analysis can be performed freely from any other conditions. Therefore, the obtained analytical results have a very high precision, and can be sufficiently used as the standard for comparison. Moreover, since it can analyze independently of analyst's capability and the conditions in the analysis, there is an advantage to obtain exact distribution data for elemental concentration.

According to the eighth form of the present invention, the fluorescent X-ray intensity peak height (P) from an element is expressed by the decimal logarithm (log P) and concentration of the element is given by the value (log P−log S) obtained by deducting the background height (log S) independent of the kind of element. Since it is log P−log S=log (P/S), this P/S gives the concentration value of the element, so that if said fluorescent X-ray intensity peak height (P) is expressed by logarithm, concentration of an element can be derived easily. Fluorescent X-ray intensity peak height (P) changes depending on thickness of hair, and if the intensity per unit mass is N, we have P=SN, where S is a proportional constant which varies according to the thickness of hair. Therefore, in expression of decimal logarithm, P=SN is turned out to be $$\log P = \log SN = \log N + \log S$$

log S is the background height without wavelength dependency in fluorescent X-ray spectra. Therefore, if the fluorescent X-ray intensity peak height (P) from an element and the background height are expressed by the decimal logarithm log P and log S, respectively, the concentration log N is given by log N=log P−log S. As mentioned above, this log N or N is equivalent to the concentration of element. In this way, we obtain concentration independently of hair thickness and shape.

According to the ninth form of the present invention, concentration of element for a subject is written as subject concentration (log P−log S), concentration of the element for healthy persons is written as healthy person concentration (log P−log S)st, and the normalized concentration M for a subject is defined by the formula $$\log M = (\log P - \log S)/(\log P - \log S)st.$$

The normalized concentration is evaluated by using the homeostatic level as a unit and is suitable for comparing elements having high and low homeostatic concentration levels.

Furthermore, if the normalized concentration M of other specimen (of the same person) is obtained, the relation between the concentration of element of hair and the concentration of element of other specimen becomes clear. Of course, concentrations of element can be obtained, free from the errors due to hair thickness variations. Consequently, deviations from the homeostatic value can be quantified and the clear and objective evaluation of physical conditions can be performed.

According to the tenth form of the present invention, trace elements important for life activity such as Ca, Fe, Cu, Zn, Se, Sr and Rb are detected, their contents are measured, and the physical conditions can be evaluated from variations of the contents of elements. Ca is not only an important element constituting the body frame, but also a very important signal transmitter of cells. It has been found that the intracellular amount of Ca increases conversely when calcium is deficient. Therefore, if the variation of the amount of Ca is measured, the evaluation of physical conditions can be performed. Moreover, when metallic element such as Fe, Cu, and Zn is superfluous, liver has a function to excrete the element, so that when the function deteriorates, the contents of these elements in hair change. Moreover, trace elements such as Se, Sr, and Rb are closely connected with regulation and homeostasis of various living body functions such as high order function of central nervous system, metabolism, immunity, and oxidation stress. Therefore, it is possible to evaluate the physical conditions by measuring the variation of contents of the elements. In particular, if the amount of Ca contained in hair is measured, shortage of Ca can be known easily, and illness caused by the shortage of Ca can be prevented.

According to the eleventh form of the present invention, since the excitation beam is synchrotron radiation (X-rays), X-ray fluorescence analysis with a very high precision can be performed. Since the synchrotron radiation intensity is very high, it can be used sufficiently even if it is monochromized. Therefore, highly precise X-ray fluorescence analysis with low noise is possible, and it is the best for the method evaluating for physical conditions of the present invention. Moreover, since it has high directivity and high polarization, it is very effective in elementary analysis of a minute sample like hair.

According to the twelfth form of the present invention, it is possible to diagnose breast cancer by the method for evaluating physical conditions of the present invention. Since the method for evaluating physical conditions of the present invention can analyze not only deviation of the content of element at the present time but also deviation of the content of element at a past time, it can diagnose the generation of illness, especially breast cancer, by abnormalities in calcium metabolism. In addition, by measuring the time variation in the content of element (especially, calcium concentration), it can be used for diagnosis of omen and progress of breast cancer. Furthermore, if the shortage of calcium can be recovered by the method for evaluating physical conditions of the present invention, the illness by abnormalities in calcium metabolism such as osteoporosis, hypertension, arteriosclerosis, malignant tumor and immunopathy can be prevented.

According to the 13th form of the present invention, said evaluation for physical conditions can be performed together with medical detailed examination. If abnormalities are found in the content of element contained in hair by the method for evaluating physical conditions of the present invention, much more exact evaluation for physical conditions can be performed by inspecting together with a medical detailed examination such as blood test, X-ray inspection and endoscopy. Since the method for evaluating physical conditions of the present invention can diagnose easily the change of physical conditions by only measuring the content of element contained in hair, it is possible to find the abnormalities of physical conditions still earlier by carrying out it periodically and said method is useful for prophylaxis of illness.

DESCRIPTION OF NOTATIONS

10 Electron Storage Ring
12 Synchrotron Radiation
14 Monochromator
16 Facility Separation Wall
18 Aluminum Foil
20 Vacuum Induction Path
22 Pinhole
24 Acrylic Holder
26 Hair
28 Semiconductor Detector

BEST MODE OF CARRYING OUT THE INVENTION

Embodiments of the method for evaluating physical conditions of the present invention are described in detail according to the following drawings.

X-ray fluorescence analysis is desirable for elementary analysis of head hair or body hair of the present invention. Although there are some kinds of x-ray fluorescence analysis such as X-ray fluorescence excited by X-rays, X-ray fluorescence excited by electron beam and X-ray fluorescence excited by ion beam, X-ray fluorescence analysis excited by synchrotron radiation is desirable in the present invention.

Figure 1:
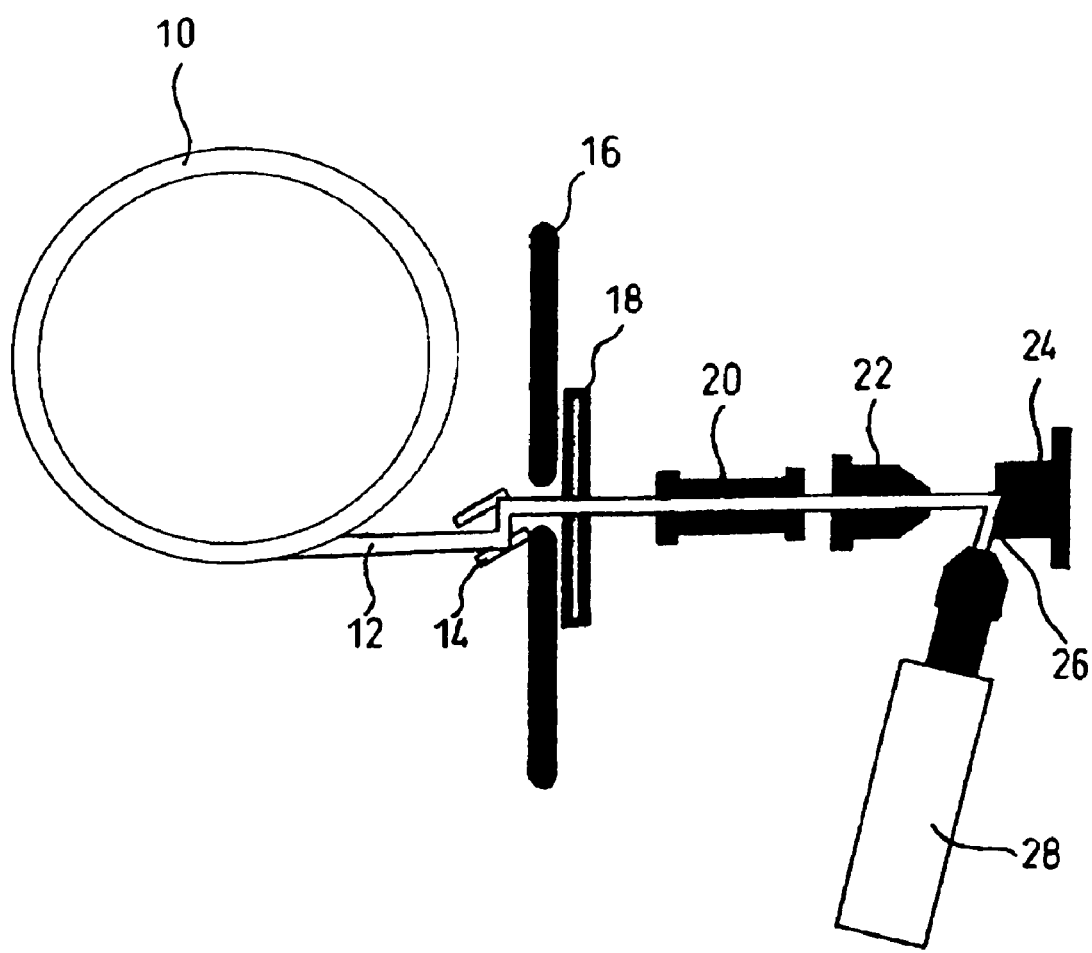
FIG. 1 is a schematic diagram of X-ray fluorescence analysis using synchrotron radiation.
Figure 2:
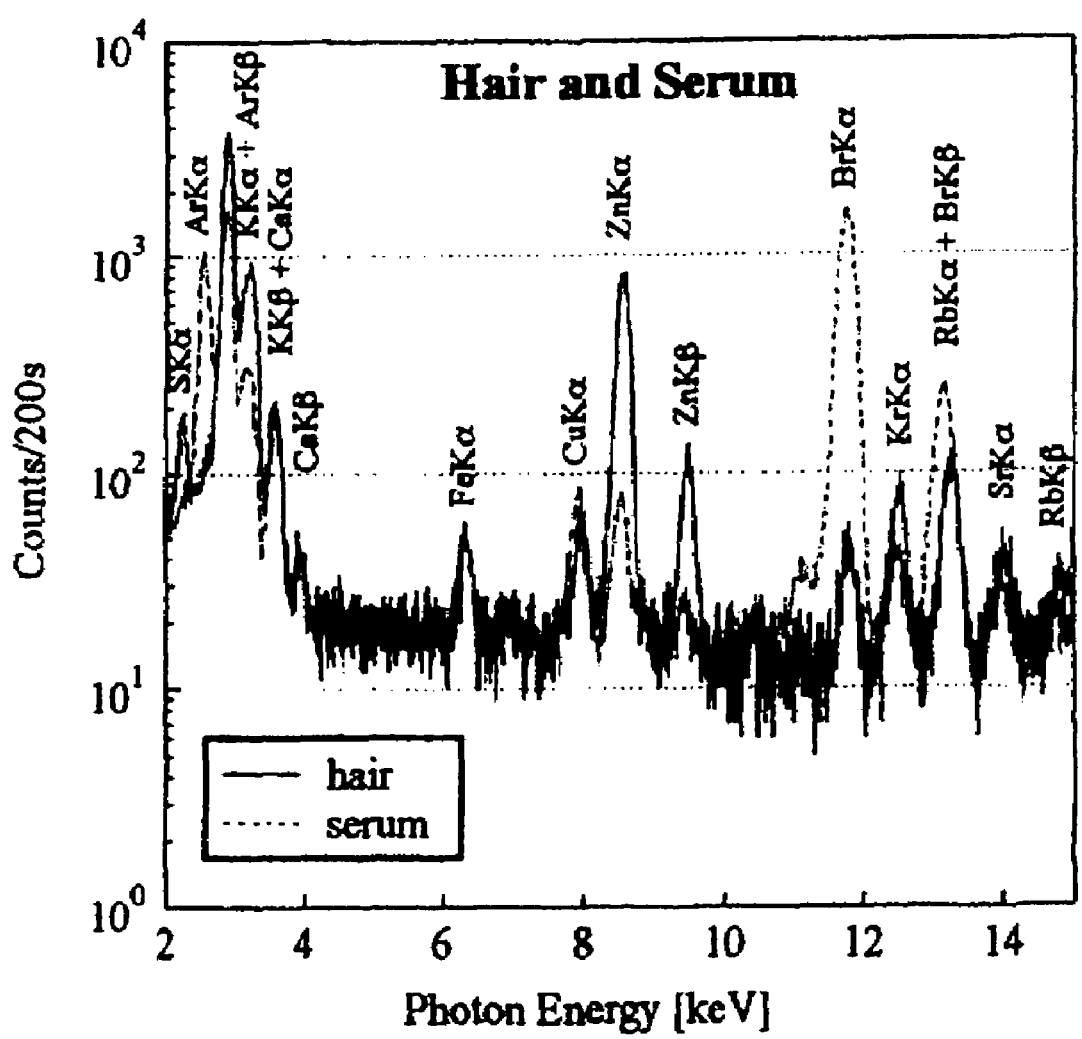
FIG. 2 is a spectrum diagram of hair and serum by the X-ray fluorescence analysis.

FIG. 1 is an illustration of the x-ray fluorescence analysis excited by synchrotron radiation. When an electron 10 accelerated to a velocity near the velocity of light changes its running direction, synchrotron radiation 12 is emitted in the tangential direction of the running orbit. This synchrotron radiation 12 is monochromatized by a monochromator (wavelength monochromater) 14, so that the X-rays of 20 keV are selected. The synchrotron radiation 12 through a radiation hole of the facility separation wall 16 sealed with an aluminum foil 18 is focused through the vacuum induction path 20 into a narrow beam by the pinhole 22 (for example, 0.2×0.2 mm), and irradiates the sample hair 26 on the hole in the center of the acrylic holder 24. The measurement part of hair is placed at the center of the hole so that the background noise is not increased. Fluorescent X-rays are emitted from the hair 26 and are detected with a semiconductor detector (SSD) 28. The detected fluorescent X-rays are resolved into photon energy (wavelength) spectrum by a multi-channel pulse height analyzer, and the number of photons within a fixed time (for example, for 200 seconds) is measured. In general, the synchrotron radiation is the linearly polarized light in the horizontal plane, so that the intensity of scattered X-rays becomes zero theoretically in the direction perpendicular to the incident direction on this plane of polarization. Therefore, the S/N ratio is improved by measuring the fluorescent X-rays emitted in this direction. FIG. 2 is an example in this way.

FIG. 2 shows spectra of head hair (Hair) and blood serum (Serum) obtained by the X-ray fluorescence analysis. The axis of abscissa expresses the energy (Photon Energy: keV) of fluorescent x-rays, and the axis of ordinate expresses the decimal logarithm of the number of photons for 200 seconds (Counts/200 s). Head hair and body hair are produced from the hair matrix cell in the hair follicle, and the hair follicle is surrounded by blood vessels, so that hair grows by nutrition supplied from blood (blood serum). Then, in order to investigate the relation of the concentration of element between blood serum (Serum) and head hair (Hair), hair and blood were simultaneously extracted from eight healthy subjects. The blood is applied to a centrifugal separator, and the blood serum was obtained by separating the erythrocyte. One drop of this blood serum is dropped on thin Mylar through which x-rays transmits easily, and it is dried. This Mylar means polyester film. X-ray fluorescence analysis of this dried blood serum and hair was performed, and in FIG. 2, their spectra are shown together so as to make their backgrounds agree with each other. T his diagram is a typical example for the case of subjects in a healthy and steady state.

In FIG. 2, the peaks of many trace elements contained in blood serum and hair are seen. The peak of zinc (Zn) in hair is higher than that in blood serum. Conversely, the peak of bromine (Br) is lower. The peaks of Ca, Fe, Cu and Sr in hair and blood serum are superimposed. In the healthy and steady state, it is found from the property of logarithm that the hair concentration of these elements is proportional to the concentration in blood serum and their proportional constants are the same. The element distributions of eight subjects in the blood serum were found to resemble in spectrum, and the spectral peaks of all the subjects are almost superimposed. It is found from these facts that these elements are important, the concentrations are always controlled under homeostasis and universal for everybody. Therefore, the concentration of element in hair is kept to be constant in the healthy case, but when it becomes unhealthy, the hair concentration deviates greatly even if it is kept at the homeostatic value in blood serum. As a result, the shift from the normal value become larger in hair.

When the height of fluorescent X-ray spectral peak of a certain element is A for thick hair and B for thin hair, the proportional relation $A=\alpha B$ holds. Here, $\alpha$ is a proportional constant, and since it is difficult to determine the value of $\alpha$ correctly, the decimal logarithm is taken. Namely, $\log A=\log \alpha B=\log B+\log \alpha$. Suppose that the concentration of the element is the same for A and B independently of thickness of hair, two peaks of log A and log B can be superimposed by shifting by $\log \alpha$.

The axis of ordinate (the number of photons) is expressed in a logarithmic scale, two spectra to be compared are superposed, and the axis of abscissa is placed so as to agree with each other. Some peaks appear on the background in the spectra. One of them is shifted upward or downward so that their backgrounds agree well. If one peak is superimposed, the element of the peak has the same concentration (the same amount of the element in 1 g of hair). If not superimposed, the difference in height between the two peaks gives how many times the concentration is different.

If the height of a spectral peak is written as log P and the background based upon x-rays scattered by the sample is written as log S, the concentration of this element is given by [log P–log S]=log (P/S). This concentration for a subject [log P–log S] is called "subject concentration", and the standard value for the healthy person [log P–log S]st is called "healthy-person concentration". In order to express the shift of the subject concentration from the healthy-person concentration, the measured value [log P–log S] is normalized by the following formula, and the value of this normalized concentration M is plotted in a logarithmic scale;

[log P–log S]/[log P–log S]st=log M

Namely, the healthy standard value is turned out to be M=10. This approach loses the absolute measurement of concentration of an element, and obtains the relative measurement of concentration free from errors due to hair thickness; how many times a certain standard concentration as concentration of element contained in hair. By this method, it is possible not only to compare precisely hair spectral peaks of a large number of persons, but also to know the proportional relation between serum and hair.

There are always the growing hair and the falling hair in head hairs with a hair cycle peculiar to human being, and growth period, degradation period and resting period are usually repeated for each hair. It is well known that the growth period is three to seven years. When the cycle finishes, the hair follicle wrapping the hair root begins to prepare for the resting period, which continues for two to three weeks. Next, when hair goes into the resting period, the hair falls out after remaining in the hair follicle for a while. After the resting period continues for three to six months, it has a growth period again, so that the hair follicle is deepen to be activated, and hair grows. Therefore, it is desirable to use hair in a growth period in the elementary analysis of the present invention.

In the present invention, a narrow synchrotron radiation X-ray beam (for example, 0.2×0.2 mm) irradiate s one head hair (body hair) (or hair bundle that arranged the hair roots), and the characteristic fluorescent X-rays generated from each element are measured, so that the homeostatic concentrations of elements are found, and the health conditions is diagnosed by using the homeostatic value. Furthermore, since the head hair (body hair) grows about 10 mm in length through one month, the content of one element is measured from the hair root to the tip point, so that it is possible to diagnose the sick omen and sick progress from the content variation. Therefore if the diagnosis of physical conditions based on hair is performed periodically, for example annually, the content of the element in the hair can be measured over several years, and the change of physical conditions can be known clearly by deviations from the homeostatic value. Consequently, various illnesses caused with deviations of the content of element can be prevented. Next, the concrete diagnostic method will be described.

Figure 3:
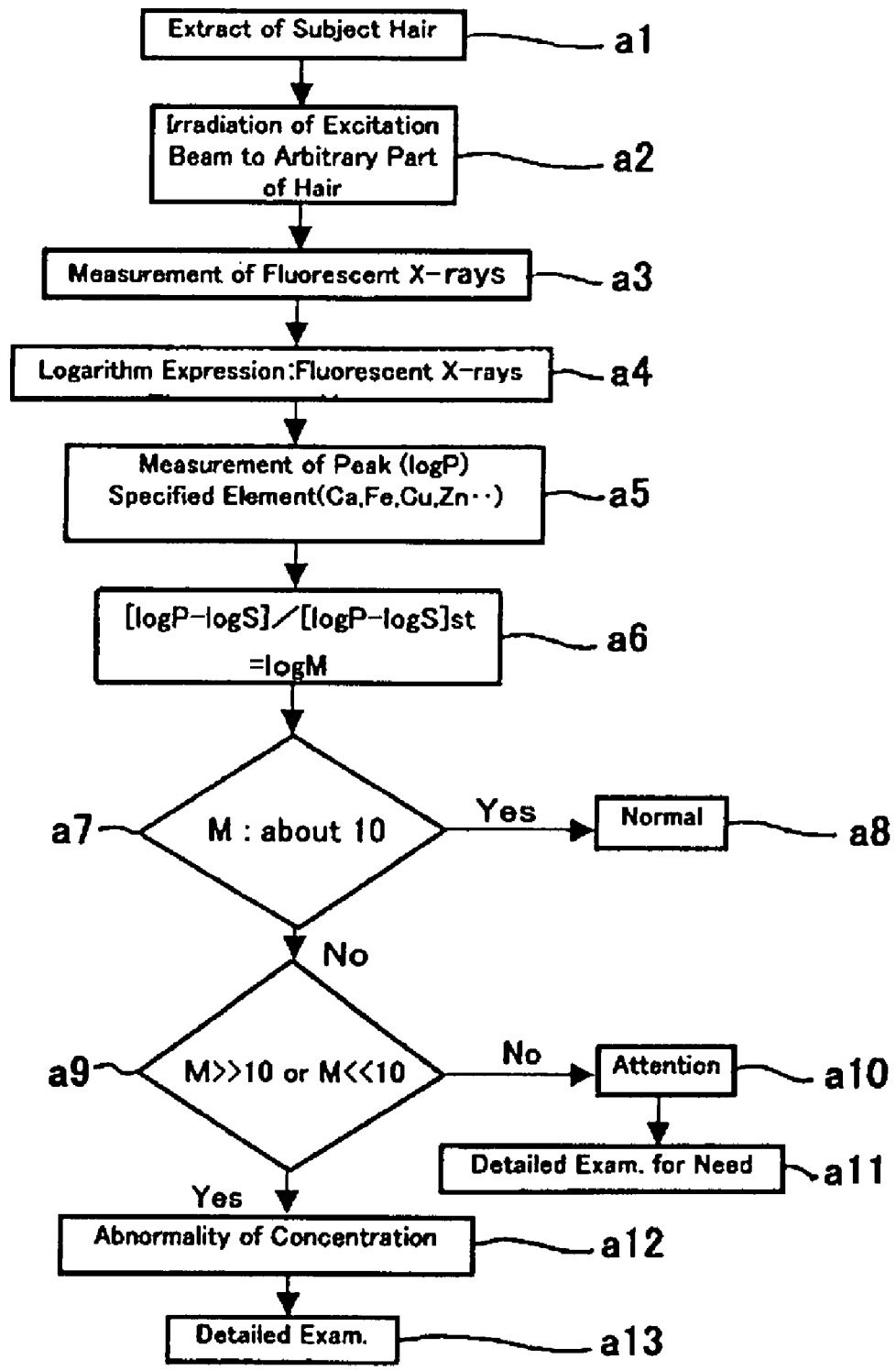
FIG. 3 is a flow diagram of the method for evaluating physical conditions to diagnose by detecting the specific element contained in hair.

FIG. 3 is a flow diagram of the method for evaluating physical conditions to diagnose by detecting specific element contained in hair of a subject. In step a1, after a hair is extracted from the subject, an arbitrary part of the hair is irradiated by the excitation beam (a2), and a spectrum of the fluorescent X-rays emitted from said arbitrary part is measured (a3), and is expressed by decimal logarithm (a4). For the spectral peak height (log P) of the specific element (a5), the ratio of the subject concentration [log P–log S] of said specific element to the standard healthy person concentration [log P–log S]st is calculated, corresponding to log M (a6). In the present invention, M is called the "normalized concentration", and when the subject is a healthy person, it turns out to be M=10. When the value of M is in the vicinity of 10, it is diagnosed to be normal (a7). When M>>10 or M<<10, it is diagnosed to be medical attention ("Care Required") (a10), and when required, a medical detailed examination (a11) may be made together. When M is deviated greatly from 10, medical detailed examination (a13) is needed as abnormalities in the concentration of element (a12). When said arbitrary part is the hair root, the current condition can be evaluated, and when it is a part distant from the hair root, it can be the condition evaluation at the time of past at which the part existed as the hair root. Thus, it is an advantage of the present invention to evaluate physical conditions at the present and at a time of past.

Figure 4:
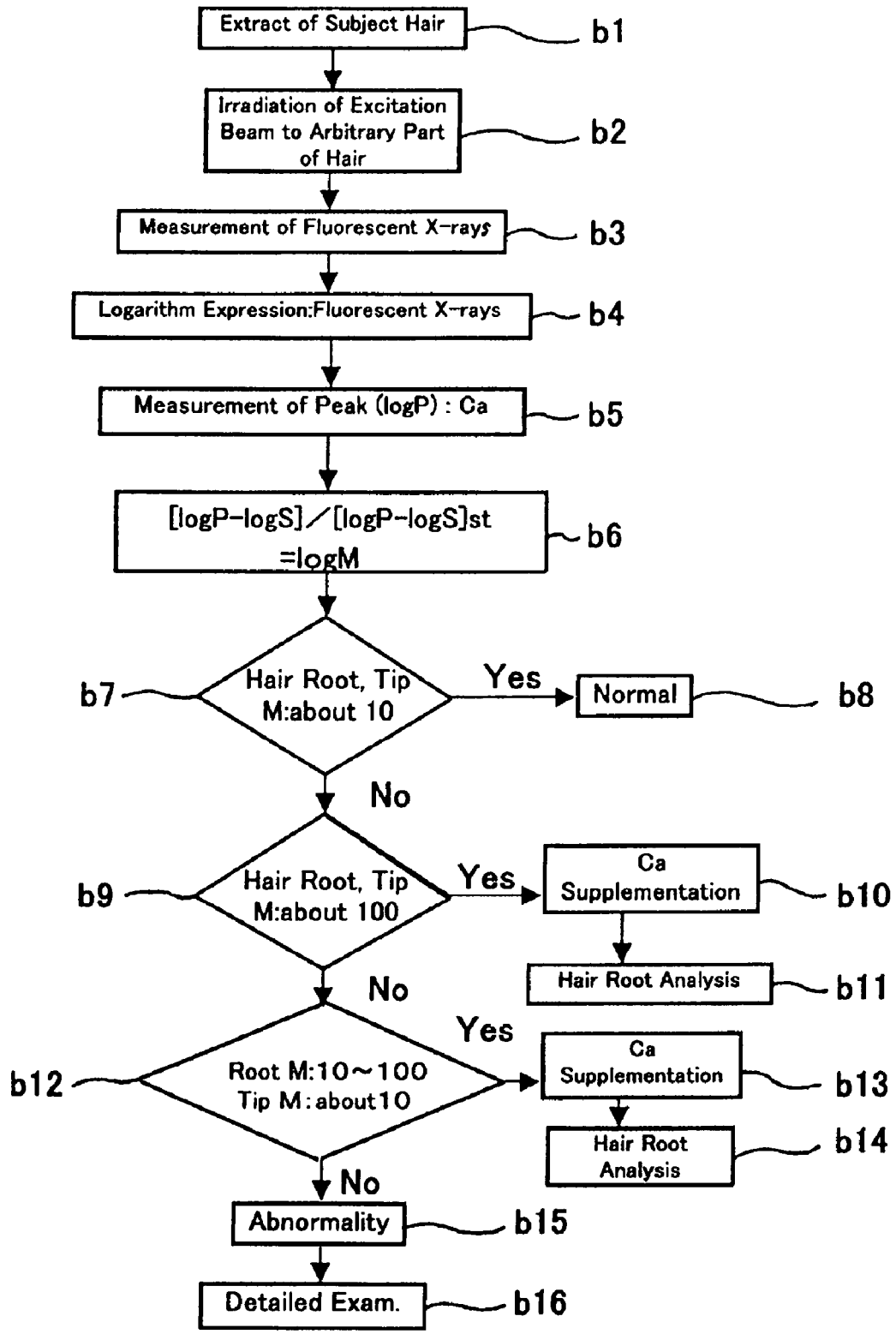
FIG. 4 is a flow diagram of the method for evaluating physical conditions to diagnose by detecting calcium element contained in hair.

FIG. 4 is a flow diagram of the method for evaluating physical conditions to diagnose by detecting calcium element contained in hair. In step b1, after a hair is extracted from a subject, an arbitrary part of the hair is irradiated by the excitation beam (b2), and the spectral distribution of the fluorescent X-rays emitted from said arbitrary part is measured (b3). The measured fluorescent X-ray spectrum is expressed by decimal logarithm (b4), the peak height (log P) for calcium element and the background height (log S) are measured (b5), and we have a ratio log M of the subject concentration of calcium [log P–log S] to the healthy-person concentration of calcium [log P–log S]st (b6). The normalized concentration M is measured for the hair root part and the tip part distant from the hair root, and the subject is diagnosed by whether both the M values are about 10 (b7). When both the values of M are in the vicinity of 10, it is diagnosed to be normal (b8). If not, it is diagnosed by whether the values of M of the hair root part and the tip part of hair are in the vicinity of 100 (b9). If both the values are about 100, the subject must take Ca supplement (Ca 900 to 1200 mg per day) for about ten days (b10). After that, a new hair root is analyzed (b11), and a detailed examination is necessary the value of M does not recovered to to the normal value (about 10). At the next step, it is diagnosed by whether the value of M of the tip part is about 10 and that of the hair root is 10 to 100 (b12). If so, the subject must take Ca supplement (Ca 900 to 1200 mg per day) for about ten days (b13), and after that, a new hair root is analyzed (b14). A detailed examination is necessary if the value of M does not recover to the normal value (about 10). When all the above cases for M are not applicable, it is diagnosed as concentration abnormality (b15). In this case, the hysteresis of M along the hair shaft is investigated, and the name of disease is found by a detailed examination (b16). Said tip part is not limited to one, and in the case of a plural number, it is possible to perform the evaluation of physical conditions in more detail. The evidence for the abnormalities of M=100 in calcium (calcium deficiency) will be mentioned later. As described later, breast cancer develops in the state that the value of M=100 for calcium continues for a long term, and the M value decreases slowly with cancer growth to the normal value M=10 during about a year. Therefore, when the tip part of hair shows M=100 and the hair root shows an intermediate value between M=10 and 100, the hair should be analyzed along hair shaft with an interval of 1-2 cm, and it should be diagnosed by investigating the variation behavior of M.

Figure 5:
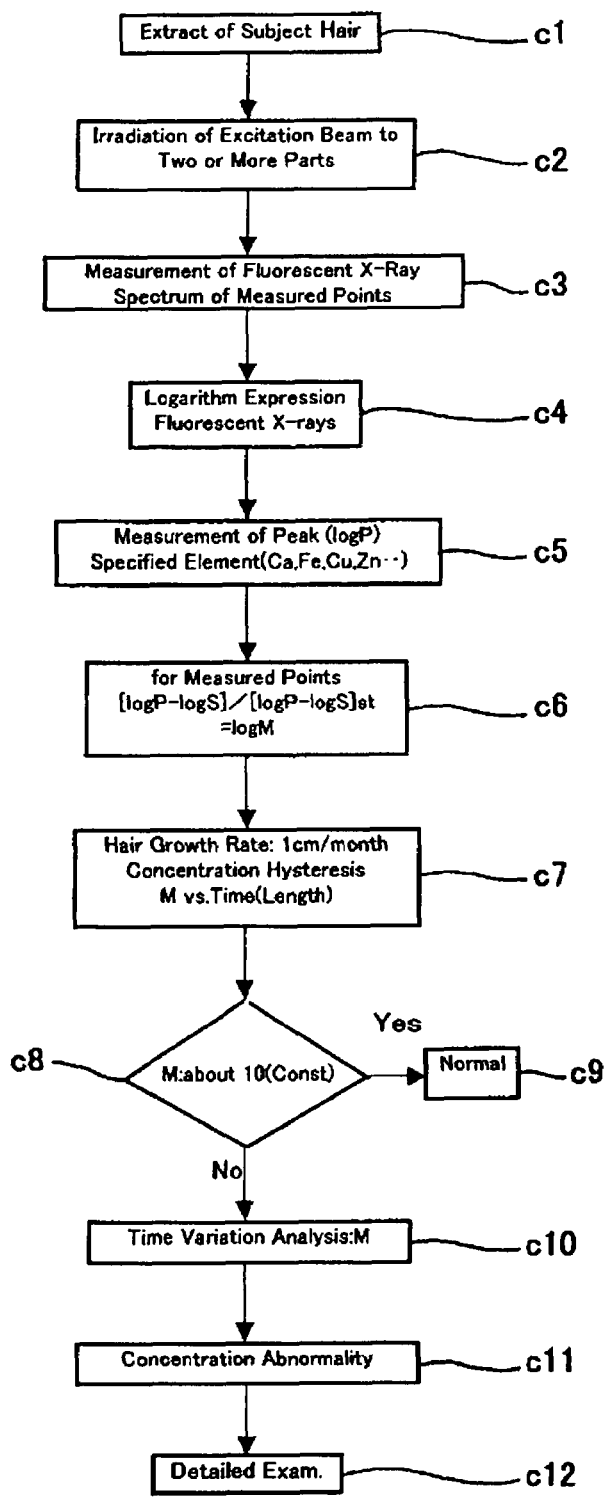
FIG. 5 is a flow diagram of the method for evaluating physical conditions to diagnose by detecting the specific element contained in two or more arbitrary parts of hair.

FIG. 5 is a flow diagram of the method for evaluating physical conditions to diagnose by detecting the specified element contained in two or more arbitrary parts of hair. In step c1, after a hair is extracted from a subject, an excitation beam sequentially irradiates two or more arbitrary parts of the hair (c2), and the spectral distribution of the fluorescent x-rays emitted from each of said arbitrary parts is measured (c3). Each of measured fluorescent x-ray spectra intensities is expressed by decimal logarithm (c4), the spectral peak height (log P) for a specific element and the background height (logs) are measured (c5), and we have a ratio log M of the subject concentration [log P–log S] of the specific element at each measured part to the healthy-person concentration [log P–log S]st of said specific element (c6). The time of past when each part existed as a hair root is found by the distance of each part from the hair root. The more the number of measured parts are, the more precisely the time variation of the concentration of element is measured, so that a more detailed diagnosis becomes possible. Although only current information can be analyzed by medical inspection such as a blood test, past information can be obtained by the hair diagnosis. Therefore, more exact diagnosis is attained by use of hair analysis together with other inspection. We can express a hysteresis curve of the concentration of element (c7), in which time (length from hair root) is plotted along the abscissa, and M is plotted along the ordinate. It is diagnosed by whether the value of M is kept at around M=10 (c8). If so, the subject is diagnosed to be normal from past to present (c9). When the concentration is deviated from M=10, time variation of the concentration of element should be analyzed (c10), and a detailed examination (c12) is needed when abnormalities in the concentration of element (c11) are found. Especially, in the case of calcium element, when both the values of M of the hair root part and the tip part of hair are in the vicinity of 100, or when the value of M of the tip part is about 10 and that of the hair root is 10 to 100, Ca supplement (Ca of 900 to 1200 mg per day) must be taken for about ten days. As a result, if the value of M does not recover to the normal value, a detailed examination becomes necessary. The illness caused by continuation of the condition of M=100 is called "calcium paradox disease" such as diabetes mellitus and Alzheimer disease, and a detailed examination for these diseases is required. As has been described in the previous paragraph, breast cancer generates in the state of M=100 and the M value decreases gradually to the normal value 10 during about one year. Therefore, in the case where the tip part shows 100 and the hair root shows the intermediate value between 10 and 100, the decay of M should be observed along the hair shaft for the early discovery of breast cancer. Besides breast cancer, for instance, large intestine cancer is also considered hypothetically to be a calcium paradox disease and has a possibility to show the similar decay along the hair shaft; a detailed examination for cancer is required.

Figure 6:
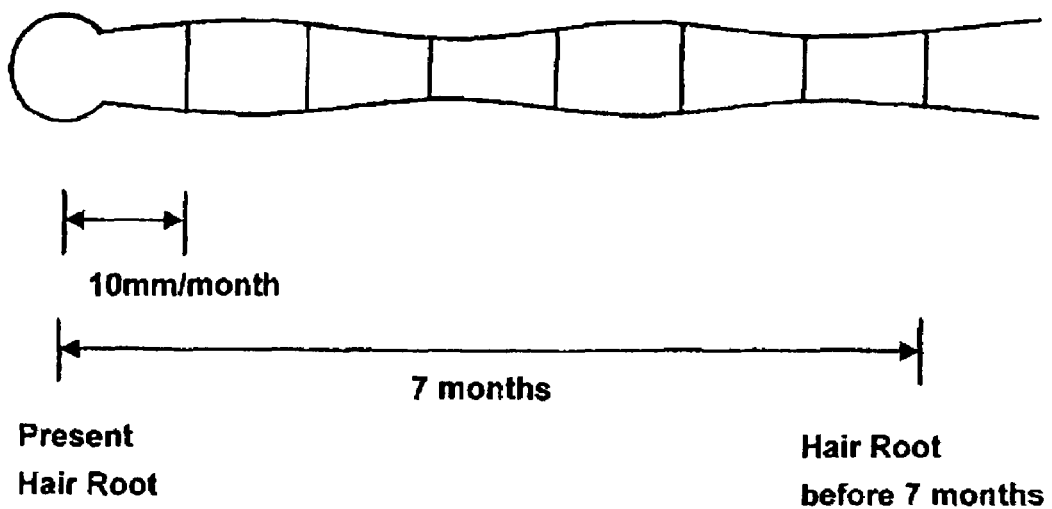
FIG. 6 is an enlarged model diagram of one hair.

FIG. 6 is a schematic illustration of one hair. Since hair grows about 10 mm in length through one month, by measuring contents of element for two or more arbitrary parts, it is possible to diagnose a sick omen and sick progress from time variation in the content. As shown in FIG. 5, if values of M for two or more arbitrary parts of hair are obtained, the time variation of M for elements can be derived from distances of the measured parts from the hair root. This is an advantage of the present invention.

Here, the relation between blood serum and hair is stated in detail. Many kinds of protein such as albumin, globulin and fibrinogen are contained in blood serum. The concentration of calcium $[Ca]_S$ in blood serum is maintained at 10 mg/dL. The one half is included in the protein (mainly albumin), the protein has a concentration of 4 to 5 g/dL, and the protein of 1 g contains calcium of 1 mg. The remaining one half exists as calcium ion $Ca^{2+}$. That is, the total calcium concentration $[Ca]_S$ in blood serum is the sum of the ion concentration $[Ca]_I$ and the concentration $[Ca]_P$ included in the protein phase, and is expressed by $[Ca]_S=[Ca]_I+[Ca]_P$.

Since calcium ion plays the role of signal transmission, the calcium ion concentration $[Ca]_I$ is controlled to be fixed strictly in any cases, namely it is kept constant as $[Ca^{2+}]=[Ca]_I$. On the other hand, $[Ca]_P$ varies to some extent. According to the knowledge of calcium paradox, generally, a cell has calcium pumps and calcium ion channels in cell membrane. The pumps are always working in order to pump Ca out of the cell, and in calcium enough, the $Ca^{2+}$ channels are closed, so that the intracellular calcium ion concentration is maintained at almost zero.

On the other hand, hair is made by hair matrix cells in a hair follicle surrounded by blood vessels, and is growing with a rate of about 0.3 mm per day. In a cell, generally, there are storage sources of calcium such as endoplasmic reticulum and mitochondria. However, in steady-state growth of hair, the concentration of element in hair must balance with supply from blood independently of the internal calcium sources of hair matrix cells. Here, the calcium concentration in hair is considered phenomenalogically.

In calcium enough, the $Ca^{2+}$ channels are closed and only the protein carrying one half of the calcium concentration $[Ca]_S$ in blood serum is taken into the hair matrix cells. Even if the process in which hair is grown up is complicated, in steady-state growth, the calcium concentration in hair $[Ca]_{HE}$ is in agreement with supply from blood serum. Namely, it is proportional to the calcium concentration $[Ca]_P$ in the protein phase of blood serum. The formula (1) holds using a proportional constant k.

$$[Ca]_{HE}=k[Ca]_P \quad (1)$$

Since $[Ca]_P$ is one half of $[Ca]_S$, it is in agreement with the result $[Ca]_{HE} \propto [Ca]_S$ of FIG. 7 as mentioned later.

With Ca deficiency, parathyroid hormone PTH is secreted and makes the $Ca^{2+}$ ion channels open. Although the protein is taken into as mentioned above, Ca in the protein phase dissolves into the liquid phase in the hair matrix cell, and Ca is also supplied from the liquid phase of serum through the ion channels, so that the Ca in the protein is in equilibrium with the ion concentration in serum through the ion channels. That is, $[Ca^{2+}]=[Ca]_I$ holds in the cell. Therefore, $[Ca]_I$ determines the calcium atom concentration $[Ca]_{PC}$ in the protein phase of the hair matrix cell. Then, the equilibrium relation between $[Ca]_I$ and $[Ca]_{PC}$ is considered.

Figure 7:
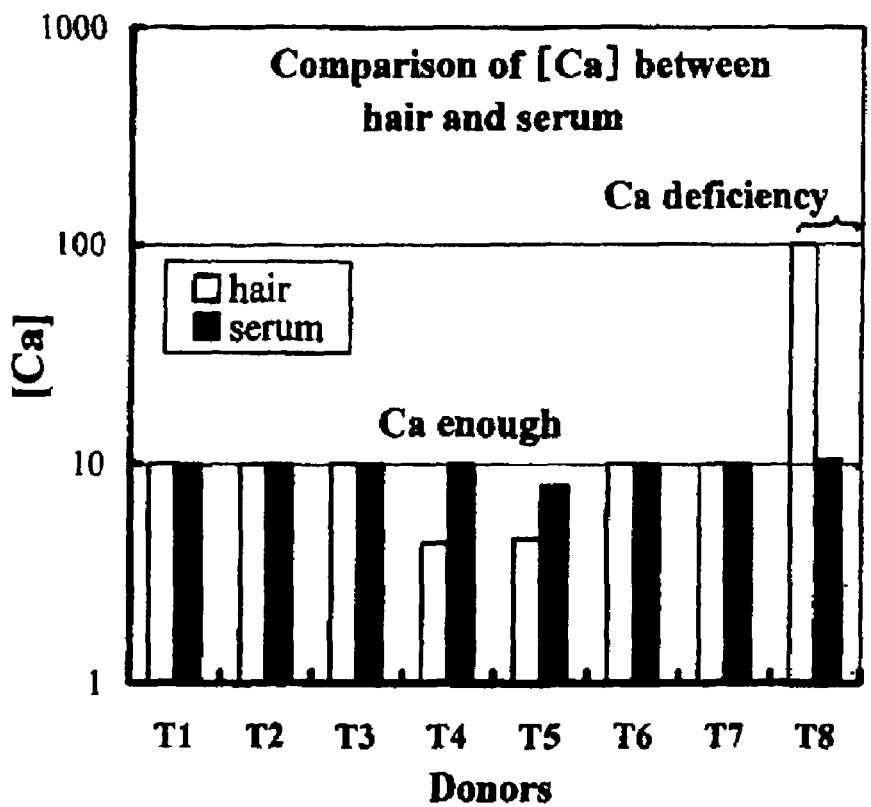
FIG. 7 is a comparison diagram of concentrations of calcium contained in hair and blood serum of eight healthy persons.
Figure 8:
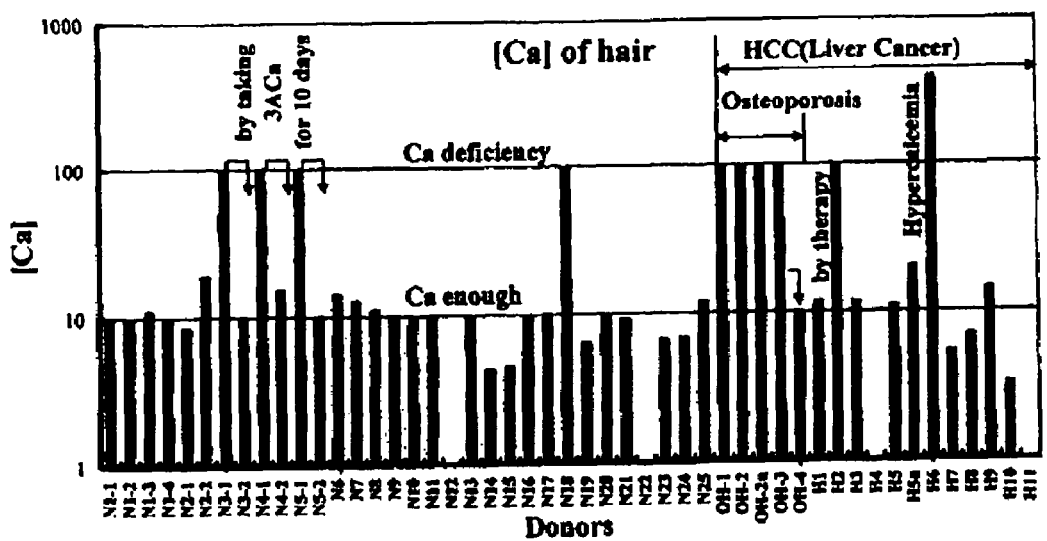
FIG. 8 is a comparison diagram of concentrations of calcium contained in hair of 37 subjects.

In the case of calcium deficiency, it is shown by FIG. 7 and FIG. 8 as will be mentioned later that the hair calcium concentration $[Ca]_{HD}$ is proportional to the square of $[Ca]_S$. This suggests that Ca atoms are incorporated into the protein phase with forming pairs of Ca atoms.

The reaction rate that makes the pair of Ca atoms is proportional to the collision probability of calcium ion $Ca^{2+}$, and the dissociation rate of Ca atom in the protein phase is proportional to the concentration $[Ca]_{PC}$. Since these two rates become equal in chemical equilibrium, it can be written as $r[Ca]_{PC}=q[Ca]_I^2$ using proportional constants r and q. Namely, it is written as $[Ca]_{HD}=k\ [Ca]PC=k(q/r)\ [Ca]_I^2$, and is in agreement with the experimental result of $[Ca]_{HD}=[Ca]_{HE}^2$ by assuming that $q/r=1$. The relation $q/r=1$ means that the chemical potential of calcium atom contained in the protein phase of the hair matrix cell is equal to that of $Ca^{2+}$ in blood serum, and the formula (2) holds as follows.

$$[Ca]_{HD}=k[Ca]_I^2 \quad (2)$$

The formula (2) holds with $q/r=1$. Since it is $[Ca]_P \sim [Ca]_I$ in formula (1) and (2), $[Ca]_{HD}=[Ca]_{HE}^2$ is obtained, and this relation is in agreement with the result of FIGS. 7 and 8 as mentioned later.

In the case of calcium deficiency, since the calcium concentration in the protein phase of the hair matrix cell that determines $[Ca]_{HD}$ is in equilibrium with the constant $[Ca^{2+}]$ in blood serum through the calcium channels, $[Ca]_{HD}$ becomes to be constant value as having the same spectral peak height in FIG. 8 described later.

Since the average concentration of PTH in blood serum increases gradually with age, it has been considered so far that the deficiency of calcium progresses with aging. However, it is shown from the result of hair analysis that calcium control works normally even for aged people if they are healthy, and the number of persons having open Ca channels with calcium deficiency increases with aging. It was found from FIG. 8, although the number was not much, Ca deficiency occurred with about 20% of subjects over fifty yeas old, and about 5% of twenties.

<Detection of Breast Cancer>

For the early detection of breast cancer, calcified lesions (precipitates of calcium salts) are observed by X-ray mamography. The calcium source for the calcification is considered to be by the bone-resorbing activity with parathyroid hormone PTH. Unexpectedly, it is known that the calcitonin concentration in the blood serum is increased by breast cancer. This suggests that the Ca flow into the cancer site is increased by suppression of Ca overflow into cells at the whole-body scale.

Figure 13:
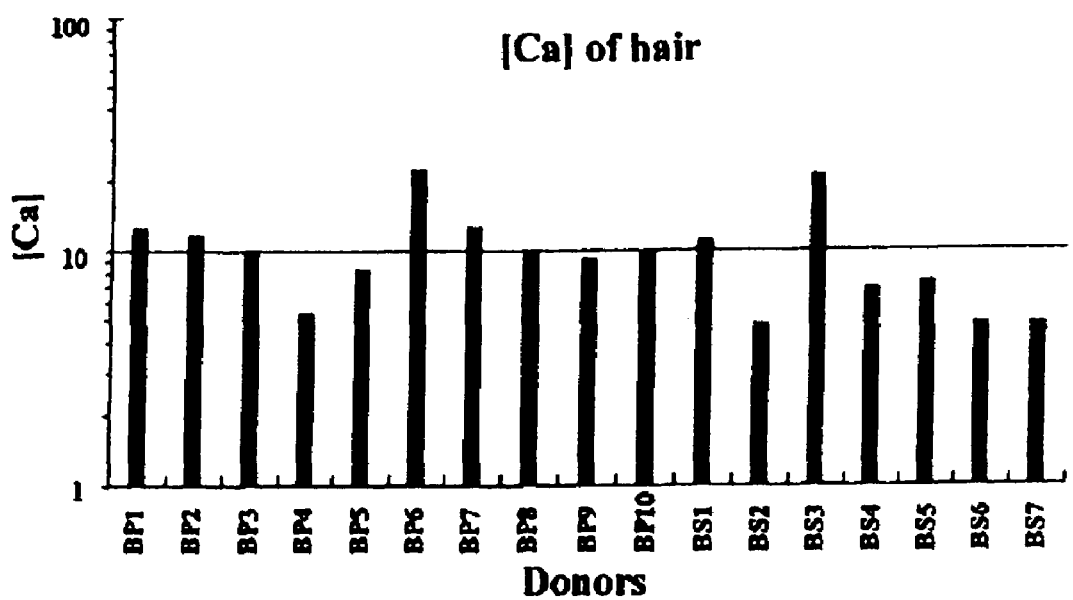
FIG. 13 is a comparison diagram of the concentration of calcium contained in hair of 17 breast-cancer patients.

As a result of analyzing the hair root from 17 breast cancer patients (metastasis to bone for 7 out of 17), as shown in FIG. 13 mentioned later, all the hair roots show the calcium concentration of normal value (lower level). As mentioned above, although the abnormal value (upper level at M=100) due to calcium deficiency is found for about 20% of general subjects over 50 years old, the result of "all the hair roots have the normal values with breast cancer" is unnatural.

Therefore, the calcium concentration has been measured from the hair root towards the tip for ten patients without metastasis to bone. As shown with typical examples in FIG. 14 mentioned later, the calcium concentration gradually increases and the hair of all the patients shows the high concentration of abnormal value at distances of 7 to 10 cm from the hair root. Beforehand, it is confirmed that the calcium concentration shows the normal value from root to tip for hair from persons in healthy steady-state life.

As seen from above results, the Ca deficiency continues over a long term before the calcification of breast cancer occurs, and the calcification is triggered with the calcium flood due to the calcium paradox. It can be concluded that the calcium concentration in hair decreases to the normal value with increase of calcitonin concentration in the blood serum.

Accordingly, by investigating the variation process of the calcium concentration of hair, a sign of breast cancer can be detected. Moreover, breast cancer may be prevented if the calcium deficiency resolves with supplements like 3ACa (Active Absorbable Algal Calcium). Women in menopause are often in Ca deficiency, and it is considered that osteoporosis and breast cancer originate from the calcium deficiency. Subjects affected by osteoporosis have hair Ca concentration at the abnormal value (the upper level at M=100), as seen from the patient labeled OH1 to OH3 in FIG.

In the following examples, the normalized [Ca] hair concentrations, M=10 and M=100, in the present measurement and normalization are referred to as the normal value (the lower level) and the abnormal value (the upper level), respectively.

Example 1

Calcium Analysis

FIG. 7 is a comparison diagram of the concentration of calcium contained in hair and blood serum of eight subjects. The subjects (Donors) are labeled on the abscissa, and [Ca]

(calcium concentration) is plotted along the coordinate. In order to compare concentrations in serum and hair, hair and blood samples are extracted simultaneously from the healthy subjects labeled T1 to T8.

Except in T5, the homeostasis is seen for the concentration $[Ca]_S$ of blood serum. The spectral peak height of concentration $[Ca]_H$ in hair is in agreement with $[Ca]_S$, except in T4, T5 and T8. That is, in the normal case, $[Ca]_H$ is proportional to $[Ca]_S$. In T8, although the blood serum has the normal $[Ca]_S$, the peak of $[Ca]_H$ of hair is very high. This high value of $[Ca]_H$ is due to Ca shortage deficiency, as seen from the experimental results for hair samples of 37 subjects shown in FIG. 8, as will be mentioned later.

The quantity of protein in blood serum fluctuates, and when healthy, the density [PP] of protein phase is 4 to 5 g/dL. Since the whole quantity of calcium contained in serum protein is nearly the same, the number of Ca atoms per one protein molecule decreases with a large [PP]. Since the number of protein molecules required to form hair of 1 g is fixed, $[Ca]_{HE}$ decreases with a large [PP]. This is the case for the subject labeled T4 of FIG. 7.

In T5, both of $[Ca]_s$ and $[Ca]_{HE}$ are lower than the normal values. This is because the quantity of Ca included in the serum protein becomes low due to the shift of pH of blood serum from the normal value. Since [Ca], is always maintained at the normal value, a 20-% decrease of $[Ca]_s$ results in a 40-% decrease of $[Ca]_{HE}$ in hair incorporating only protein.

FIG. 8 is a comparison diagram of concentration of calcium contained in hair roots extracted from of 37 subjects. The subjects are labeled on the abscissa, and [Ca] (calcium concentration) is expressed along the ordinate. Among them, 11 samples labeled H1 to H11 are from the patients of liver cancer (HCC). A patient affected by both of osteoporosis and liver cancer provided four hair samples labeled OH-1, OH-2, OH-3 and OH-4 extracted with respective intervals of four months, one month and five months. (OH-2*u* is for the part of 1 mm from hair root). The remaining 25 subjects are healthy and labeled N1 to N25. Five subjects from N1 to N5 had taken the supplement of calcium for ten days, the hair samples extracted before and after the supplementation are encoded as N1-1 and N1-2, respectively. In total, FIG. 8 shows Ca concentrations in the hair roots of 37 subjects.

In FIG. 8, most of the subjects have normalized values at around the lower level of M=10, and the upper level of $[Ca]_H$ at a normalized value M=100 is due to the Ca deficiency. The hair samples labeled N3, N4, N5, N18, OH and H2 show the peak height of $[Ca]_H$ at the upper level (M=100). It should be noted that the heights of peaks are the same by Eq. (2) due to the equilibrium with the strictly regulated serum [Ca], through the open channels of the hair matrix cells. The subjects labeled N3, N4, and N5 took supplement 3ACa (Active Absorbable Algal Calcium) with a ratio of calcium of 900 mg per day for ten days. After this supplementation, hair samples, as a result due to Hair samples extracted from these subjects were analyzed, and it was observed that the $[Ca]_H$ concentration in the hair roots decreased to the normal values at the lower level, as shown in FIG. 8. This observation confirms that the upper level of hair $[Ca]_H$ concentration is due to Ca deficiency.

The subject labeled OH has suffered from osteoporosis and HCC. The hair samples labeled OH-1 to OH-3 extracted over one year showed the $[Ca]_H$ values at the upper level, and then the $[Ca]_H$ decreased to the lower normal level by a therapy of cancer and the 3ACa supplementation. These results confirm that the upper level of the normalized M value $[Ca]_H$=100 corresponds to Ca deficiency. It is considered that the very high Ca concentration in the hair of H6 is due to hypercalcemia caused by PTHrP secreted from the tumor.

The above results are summarized as follows: The Ca deficiency can be detected easily by X-ray fluorescence analysis of hair, and It becomes clear that (1) in Ca enough, the calcium concentration $[Ca]_H$ of hair shows the lower level proportional to $[Ca]_S$ of blood serum by closed Ca ion channels in cells and (2) in Ca deficiency, the $[Ca]_H$ has the upper level proportional to the square of $[Ca]_S$ by open Ca channels in cells.

Example 2

Iron Analysis

Figure 9:
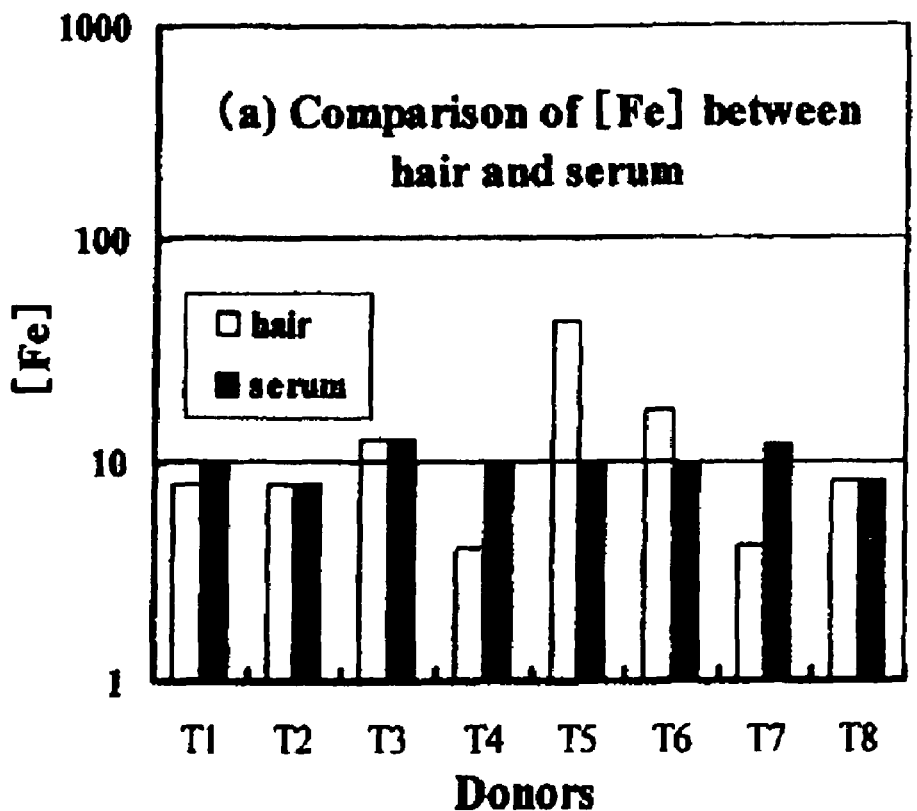
FIG. 9 is a comparison diagram of concentrations of iron contained in hair and blood serum of eight healthy persons.

FIG. 9 is a comparison diagram of concentration of iron contained in hair and blood serum of eight healthy subjects. The subjects (Donor) are labeled on the abscissa, and [Fe] (iron concentration) is plotted along the ordinate. The concentrations for T4 correspond to the case where the density [PP] of protein phase in blood serum is large, as has been described for T4 of FIG. 7. This means that Fe exists in serum protein and inflows into hair with the protein in the same way as Ca in the case of closed Ca ion channels.

Figure 10:
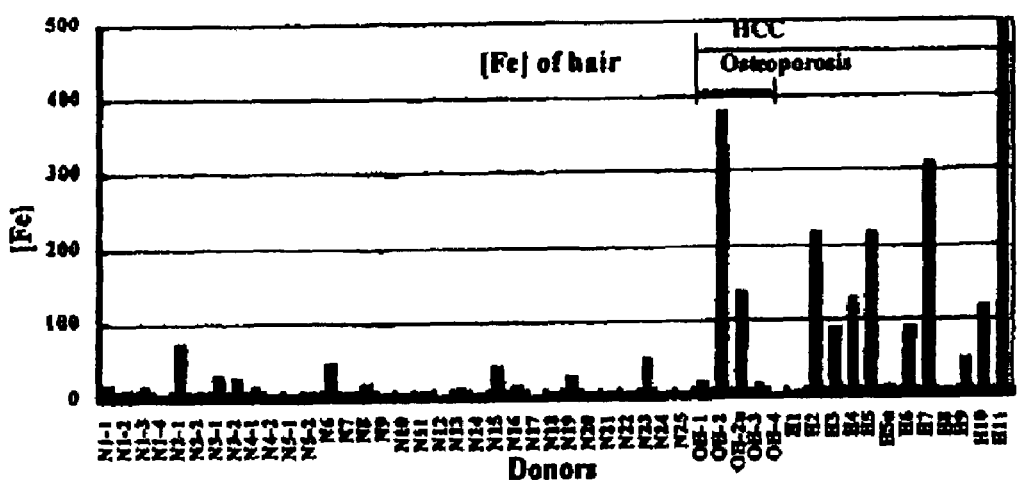
FIG. 10 is a comparison diagram of concentrations of iron contained in hair of 37 subjects.

FIG. 10 shows concentrations of iron contained in hair roots from the 37 subjects. The subjects (Donor) are labeled on the abscissa, and [Fe] (iron concentration) is plotted along the ordinate. There are ten or more subjects having abnormal iron concentrations even in the 25 healthy subjects. Such a high [Fe] in hair may indicate production of active oxygen (toxicity, carcinogen) because of a close association between ion and active oxygen. It is remarkable that most of the patients (9 out of 11) of liver cancer (hepatocellular carcinoma, HCC) have abnormally high Fe concentrations due to deterioration of the liver function to excrete metals into bile.

Example 3

Copper Analysis

Figure 11:
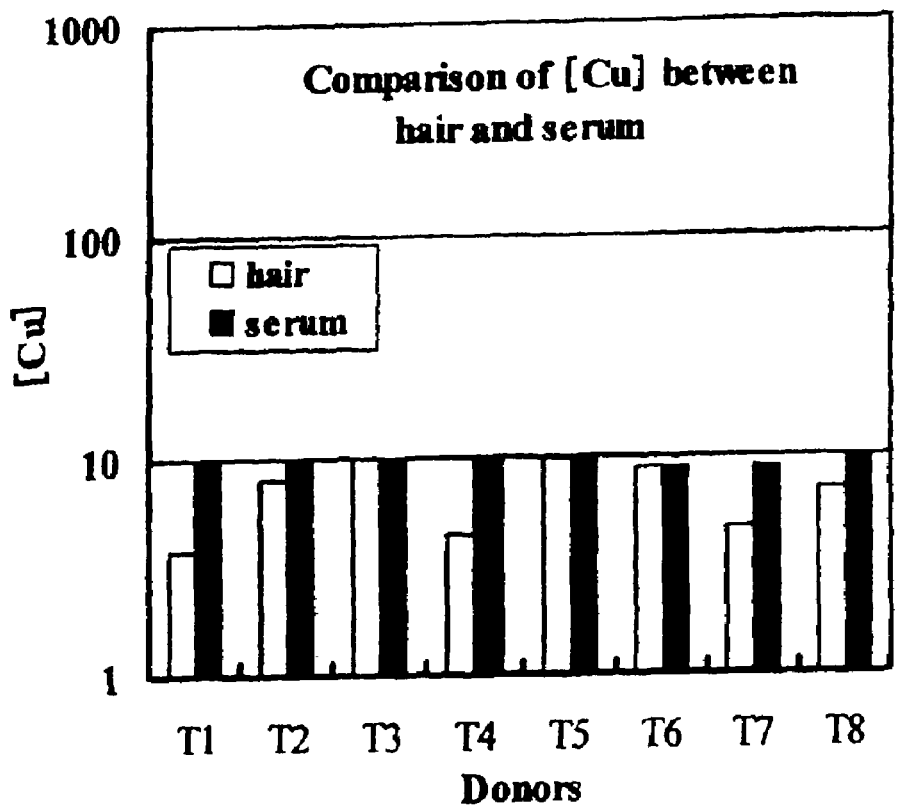
FIG. 11 is a comparison diagram of concentrations of copper contained in hair and blood serum of eight healthy persons.

FIG. 11 is a comparison diagram of concentration of copper contained in hair and blood serum of eight healthy subjects. The subjects (Donor) are labeled on the abscissa, and [Cu] (copper concentration) is expressed along the ordinate. The concentrations for T4 correspond to the case where the density [PP] of protein phase in blood serum is large, as has been described for T4 of FIG. 7. This means that Cu exists in serum protein and inflows into hair with the protein in the same way as Ca in the case of closed Ca ion channels.

Figure 12:
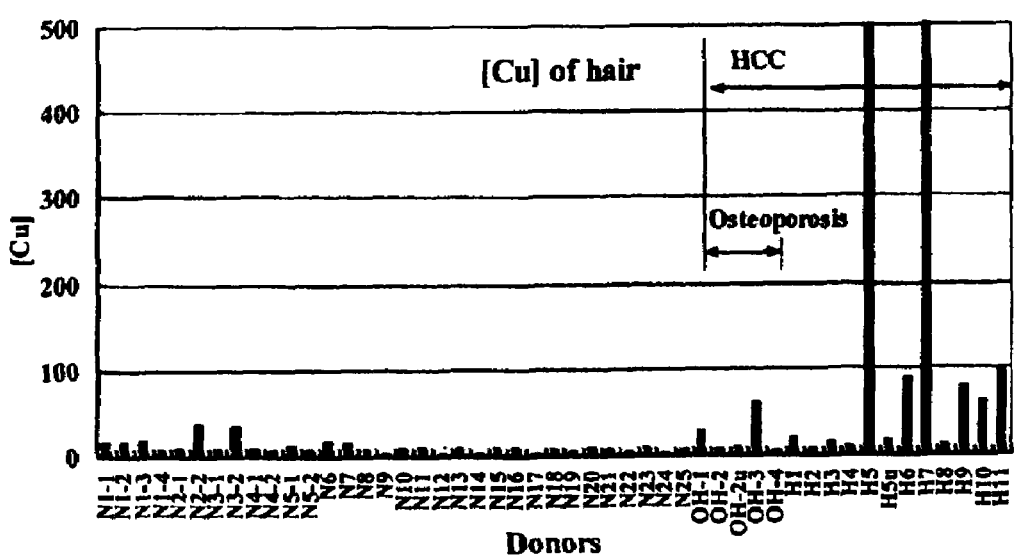
FIG. 12 is a comparison diagram of concentrations of copper contained in hair roots of 37 subjects.

FIG. 12 shows concentrations of copper contained in hair roots of the 37 subjects. The subjects (Donors) are labeled on the abscissa, and [Cu] (copper concentration) is plotted along the ordinate. It should be noted that many patients (6 out of 11) of liver cancer have abnormally.

Example 4

Breast Cancer

FIG. 13 shows concentrations of calcium contained in hair roots of 17 breast-cancer patients. Patients (Donors) are labeled on the abscissa, and [Ca] (calcium concentration) is the ordinate. Among them, the patients labeled BP1 to BP10 are of primary cancer, and the remaining samples BS1 to BS7 are from patients with metastasis to bone.

As illustrated in FIG. 13, all the 17 patients of breast cancer showed the calcium concentration at the lower level (normal values). For the patients without metastasis to bone, calcium concentration was measured towards the tip from the hair root.

Figure 14:
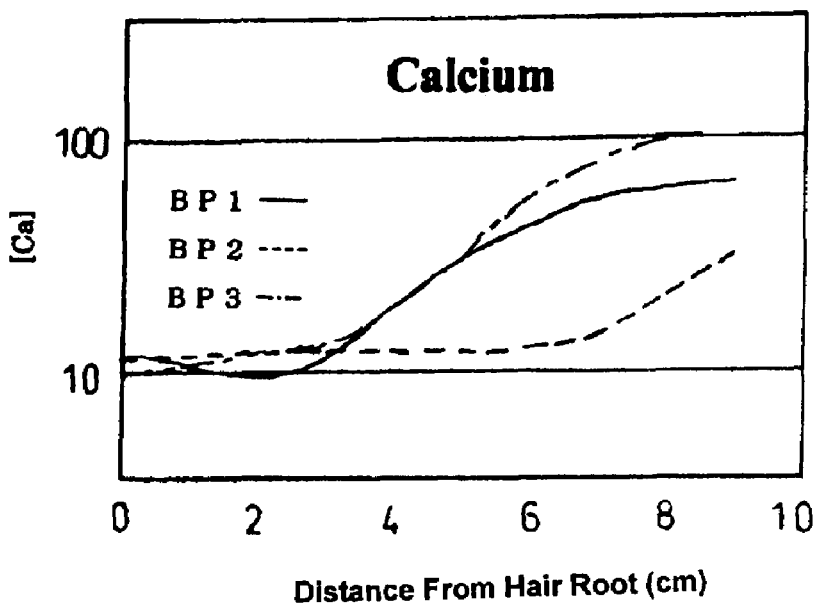
FIG. 14 is a hysteresis curve diagram of the concentration of calcium contained in hair from hair root to tip of hair.
Figure 15:
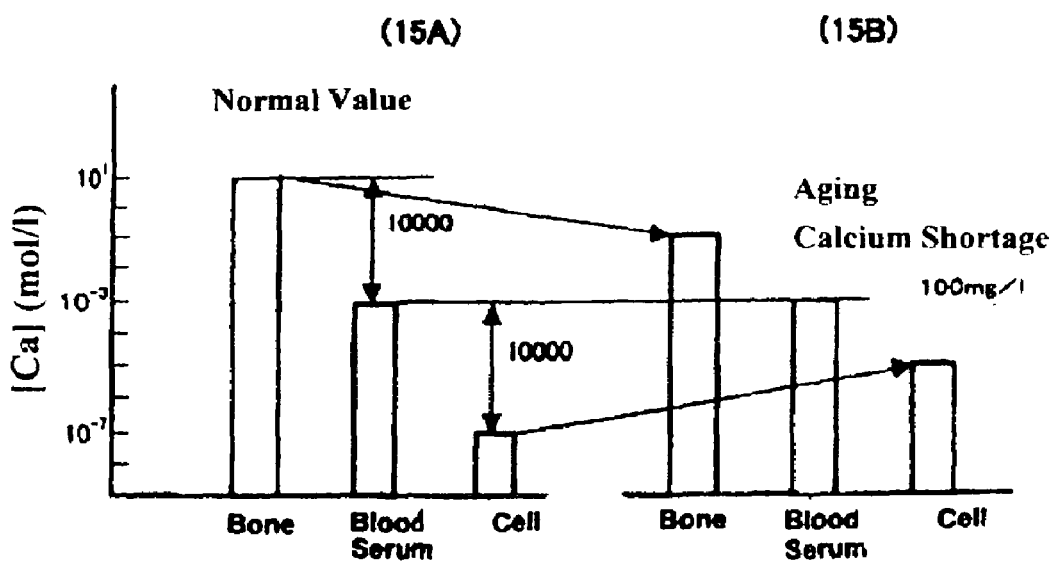
FIG. 15 is an explanatory diagram for outline of calcium paradox.
Figure 16:
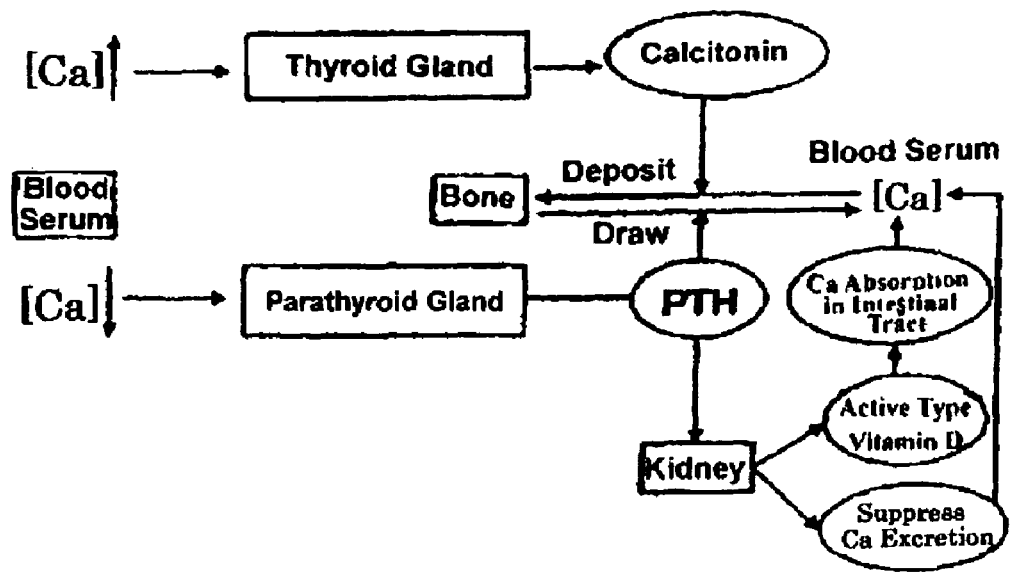
FIG. 16 is an explanatory diagram showing the mechanism by which the concentration of calcium [Ca] in blood is under homeostatic control.
Figure 17:
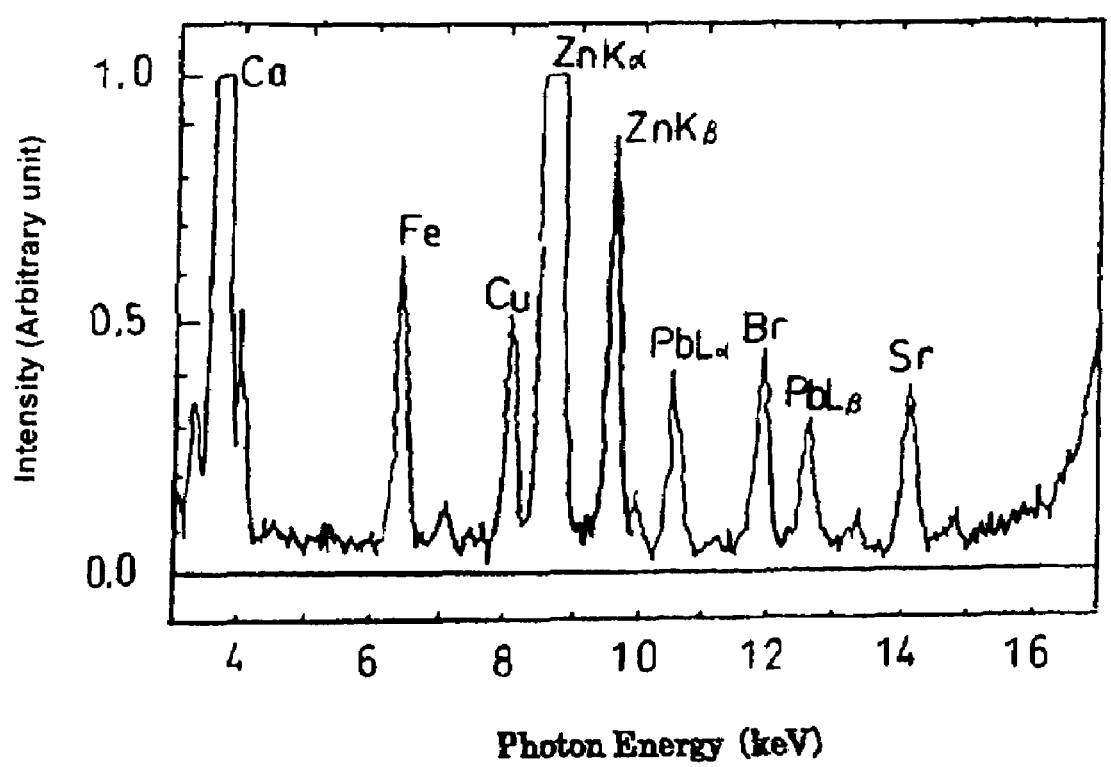
FIG. 17 is an x-ray fluorescent spectrum of elements contained in a hair root shown in patent reference 1.

FIG. 14 shows the hysteresis curves of concentration of calcium contained in shafts form root to tip for the 3 patients of breast cancer labeled BP1, BP2, and BP3 without metastasis to bone. The distance (cm) from the hair root is expressed along the abscissa, and [Ca] (calcium concentration) is plotted along the ordinate. As illustrated in FIG. 14, calcium concentration increases slowly with the distance from the root and all the hair from the patients shows the abnormal high values at distances of 7 to 10 cm apart from the hair root. Beforehand, it is confirmed that healthy subjects have the normal hair calcium concentrations at the lower level from the hair root to the tip. It is possible to diagnose omen and generation of breast cancer by use of such a hysteresis curve diagram of hair calcium concentration.

It is proved from examples 1, 2, 3 and 4 that the method for evaluating physical conditions of the present invention can detect easily abnormalities in mineral metabolism, especially the calcium deficiency, and can prevent various illnesses caused from calcium deficiency. For a trace element such as Fe and Cu, an exact diagnosis can be made by comparison with the concentration of element of other specimens such as serum and by the time variation in their concentration observed along a hair shaft.

Elemental concentration in specimens such as hair and serum is employed for the diagnosis in the present invention. To avoid any errors from specimen thickness, the relative concentration [log P−log S] has been measured, instead of the absolute concentration. Also, we can employ the normalized concentration (M or log M) defined by [log P−log S]/[log P−log S]st=log M as a concentration value free from the specimen-thickness effect, although M or log M depends on the instrument used through log S (The absolute concentration is not necessary for the diagnosis). Any other definition for concentration and normalization approaches are also useful if mutual comparison in concentration between a subject and the healthy standard subject is possible by making the specimen-thickness effect minor. For example, the absolute concentration expressed by the number of atoms per unit volume or unit weight can be adopted if is precise enough. It is needless to say that not only the fluorescent X-ray intensity but also any other concentration measurements such as mass spectroscopy, element weight, element mol number, the number of atom, electric resistance, dielectric constant and magnetism are applicable for said concentration of element can be employed. Also, it is needless to say that the present invention is not limited to the above-described embodiments; and various modifications and design changes, etc. are included in the scope of the present invention within this limits which do not deviate from the technical spirit of the present invention.

INDUSTRIAL APPLICABILITY

The method for evaluating physical conditions of the present invention enables us to measure relative concentrations of element in a logarithmic scale precisely, independently of the specimen size and mass. Therefore, precise comparison and relation of elemental concentrations in different kinds of materials such as hair and serum are realized; concentration variations along a single hair shaft can be observed directly, although losing information on the absolute concentration. The present analytic method is expected to be useful in various fields such as medicine and biochemistry.

The invention claimed is:

1. A method of evaluating a physical condition of a test subject comprising the steps of:
   (a) extracting at least one hair from a subject;
   (b) performing X-ray fluorescence analysis on at least one point of said at least one hair;
   (c) measuring a spectral peak value (P) of calcium (Ca) and a background value (S) from said X-ray fluorescence analysis;
   (d) obtaining a [Ca] concentration value of a person expressed by the formula (1);

$$\log[Ca]=[\log P-\log S] \tag{1}$$

(e) performing steps (a) through (d) on a plurality of healthy persons and/or persons with Ca supplementation to establish a homeostatic standard lower level of Ca concentration in hair (st) with closing of Ca ion channels of cells expressed by the formula (2), $$\log[Ca]st=[\log P-\log S]st, \tag{2}$$

which is derived from Ca in serum protein by the principle that the content of an element in the hair must be equal to the inflow of that element into the cells of the hair root from serum;
   (f) performing steps (a) through (d) on a plurality of persons with Ca deficiency characterized by the tendency for people over 50 years old to have Ca deficiency to establish another homeostatic upper level of Ca concentration in hair (up) with opening of Ca ion channels of cells expressed by the formula (3), $$\log[Ca]up=[\log P-\log S]up, \tag{3}$$

which is derived from the homeostatic serum Ca ion concentration by said principle and is larger enough for separating [Ca]up from [Ca]st;
   (g) performing steps (a) through (d) for a person whose health is being evaluated as said test subject to establish a Ca concentration value for the evaluated person expressed by the formula (1);
   (h) comparing said Ca concentration value of said person whose health is being evaluated with said lower level of the formula (2) and upper level of formula (3) to determine whether Ca channels of cells are closed or open for evaluating the health.

2. The method of evaluating physical conditions according to claim 1 wherein cancer is protected and/or detected by the characteristics that cancer is generated when the hair Ca concentration expressed by the formula (1) is at said upper level of the formula (3) and that said hair concentration decreases gradually to said lower level of the formula (2) with cancer growth.

* * * * *